(12) United States Patent
Kennedy et al.

(10) Patent No.: US 11,125,750 B2
(45) Date of Patent: Sep. 21, 2021

(54) METHODS, ASSAYS AND KITS FOR DETECTING EXPOSURE TO CYANOTOXINS (71) Applicant: The University of Toledo, Toledo, OH (US)

(72) Inventors: David Kennedy, Toledo, OH (US); Steven Haller, Toledo, OH (US); R. Mark Wooten, Toledo, OH (US); Deepa Mukundan, Toledo, OH (US); Apurva Lad, Toledo, OH (US); John Presloid, Toledo, OH (US); Jason Huntley, Toledo, OH (US); Bruce Levison, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/454,327

(22) Filed: Jun. 27, 2019

(65) Prior Publication Data

US 2020/0003775 A1    Jan. 2, 2020

Related U.S. Application Data (60) Provisional application No. 62/691,036, filed on Jun. 28, 2018.

(51) Int. Cl.
*G01N 33/53* (2006.01)
*G01N 33/569* (2006.01)
*C12Q 1/04* (2006.01)
*G01N 33/18* (2006.01)
*G01N 33/563* (2006.01)

(52) U.S. Cl.
CPC ......... *G01N 33/56911* (2013.01); *C12Q 1/04* (2013.01); *G01N 33/1826* (2013.01); *G01N 33/563* (2013.01)

(58) Field of Classification Search
CPC .................................................. G01N 33/56911
See application file for complete search history.

(56) References Cited

U.S. PATENT DOCUMENTS

| | | | |
|---|---|---|---|
| 5,968,751 A * | 10/1999 | Griffin | C12N 9/647 435/7.1 |
| 6,967,240 B1 | 11/2005 | Dietrich et al. | |
| 2011/0045606 A1 | 2/2011 | Kennedy | |
| 2013/0337469 A1 | 12/2013 | Kennedy | |
| 2014/0349880 A1 * | 11/2014 | Qiu | C07K 16/00 506/9 |

OTHER PUBLICATIONS

Heussner et al (Chemico-Biological Interactions vol. 223, pp. 10-17) (Year: 2014).*

* cited by examiner

*Primary Examiner* — Albert M Navarro
*Assistant Examiner* — Mark Navarro
(74) *Attorney, Agent, or Firm* — MacMillan, Sobanski & Todd, LLC (57) ABSTRACT

Methods and kits for the detection of toxic cyanobacteria in a sample by analyzing the sample for the presence antibodies raised in a host, where the presence of antibodies is indicative of toxic cyanobacteria, are described.

10 Claims, 6 Drawing Sheets
(6 of 6 Drawing Sheet(s) Filed in Color)

Anti-ADDA antibodies in the plasma sample

METHODS, ASSAYS AND KITS FOR DETECTING EXPOSURE TO CYANOTOXINS

CROSS-REFERENCE TO RELATED APPLICATIONS

This is application claims the priority to U.S. provisional application Ser. No. 62/691,036 filed Jun. 28, 2018, the entire disclosure of which is expressly incorporated herein by reference.

STATEMENT REGARDING FEDERALLY SPONSORED RESEARCH

This invention was not made with any government support and the government has no rights in the invention.

BACKGROUND OF THE INVENTION

Harmful algal blooms (HABs) are a large and growing environmental health concern and health care providers currently have inadequate/inconclusive means for a differential diagnosis for cyanotoxin exposure.

Harmful algal blooms are the result of eutrophication of bodies of water, and are caused by phosphates and nitrates from pollution. These HABs contain *Anabaena, Microcystis, Nostoc*, and *Planktothrix*

One of the by-products of harmful algal blooms (HAB's) are toxins produced by cyanobacteria termed "cyanotoxins." Cyanotoxins (such as microcystins) are responsible for much of the human and animal health concerns associated with HAB's. Currently, there is no laboratory diagnostic testing which can confirm the presence of cyanotoxins in human clinical specimens.

This is of grave concern because these microcystins are hepatotoxins that may cause failure of the liver. There are many routes of exposure to such microcystins, such as ingestion, inhalation, and skin contact.

Harmful algal blooms are a growing regional, national, and international problem. Harmful algal blooms have occurred in every region of the United States. In 2014, 38 states responded to a survey about harmful algal blooms, and more than half reported that such blooms occur every year in a freshwater body. All coastal states have reported harmful algal blooms in marine waters, and these blooms also have been reported in all the Great Lakes. Evidence suggests that harmful algal blooms are increasing in number and severity because of changing temperatures, farming practices, storm water runoff and wastewater overflows. Lake Erie provides drinking water for over 11 million people. 70 million people recreate in the Great Lakes each year including 1.8 million licensed anglers and spend $15 billion. For example, on the western end of Lake Erie, in Toledo, Ohio, there were HABs during summer 2014; and, in August the microcystin (MC) levels of purified drinking water were ≤2.469 µg/L which is well over the 1 µg/L threshold. In Brazil, in 1996, MC-contaminated water was used for dialysis of 131 patients. 100 developed liver failure, and 52 died. There the MCs were detected in serum at levels below 0.160 µg/L. Microcystin toxicity is a special concern when there is chronic exposure to the MCs. In a 2011 study from China of 1,322 children aged 7-15 years there demonstrated abnormal liver chemistry function in studies in the group with highest daily Microcystin intake. Other studies have shown liver abnormalities with non-acute exposure.

Another concern is carcinogenicity, where, in a 1996 China study in an area where fishermen live and eat fish and fowl from a Microcystin contaminated lake, incidence of liver cancer is 30 times greater than Western Europe.

Yet another concern is abnormal spermatogenesis, where lab studies show abnormal sperm morphology and DNA abnormalities Detection of MC remains a problem. ELISA and LC-MS are the most common methods to detect and quantify the toxin levels in water samples. Public health advisories and guidelines are put up around the affected area to notify the public against the use of water for recreational or agricultural purposes.

These current tests (ELISA, LC-MS) have disadvantages as such tests are primarily designed to test the presence of toxins in water samples. If exposure is suspected there is no diagnostic test to confirm exposure or aid in differential diagnosis.

However, it is common for patients to not present to their health care provider for days or sometimes weeks after a potential exposure to cyanotoxins and by this time blood or urine levels of the toxin may be non-existent because of biological clearance or absorbance.

There is a great need for a diagnostic tool to detect the presence of the toxin/immune response in biological samples (blood, urine). This is especially of concern, as the clinical presentation may occur days to months after the exposure. Thus, being able to detect exposure after the toxin is below detectable limits in blood or urine would be a distinct advantage.

SUMMARY OF THE INVENTION

In a first broad aspect, there is a method that detects anti-Microcystin antibodies in plasma from exposed organism, including fish, reptiles and mammals.

The currently described method now provides diagnostic tests for such exposures.

The method described herein to detect the presence of antibodies against the toxins in the blood sample is also useful as a diagnostic test (in conjunction with other direct measures of toxin levels) to assist in differential diagnosis.

The method described herein has applications for human and veterinary health, wildlife surveillance, and public health/research (CDC collaboration in place)

The method described herein is also useful at the population level to study the prevalence of exposure in a population living close to a water body that has harmful algal blooms (understanding epidemiology of the disease).

In one aspect, there is provided herein a method for the detection of toxic cyanobacteria in a sample from a host, comprising: analyzing the sample for the presence antibodies raised in the host, wherein the presence of the antibodies is indicative of toxic cyanobacteria.

In one aspect, there is provided herein a method for the detection of toxic cyanobacteria in an assay, comprising: analyzing the sample for the presence antibodies complexed to an immobilized microcystin, wherein the presence of the antibodies is indicative of toxic cyanobacteria.

In one aspect, there is provided herein a method for the detection of microcystins in a sample, comprising:
  a) providing a substrate coated with a protein capable of conjugating with the ADDA region of microcystin;
  b) adding dilutions of the sample to the coated substrate;
  c) washing excess sample from the coated substrate,
  d) detecting any bound anti-ADDA antibodies from the sample using a labeled antibody; and, e) adding an enzymatic substrate to produce a visible signal, which indicates the presence of microcystins in the sample.

In certain embodiments, the antibodies detected are against the ADDA region of microcystins/nodularins, or any other ADDA containing cyanotoxin.

In certain embodiments, the sample comprises blood of a subject suspected of being exposed to cyanobacteria.

In certain embodiments, the sample comprises an environmental sample containing one or more cyanobacterial organisms.

In certain embodiments, the sample comprise salt water or freshwater.

In certain embodiments, the sample is from a blue-green algal bloom.

In certain embodiments, the sample is taken days, weeks, or longer after cyanotoxin exposure.

In certain embodiments, the toxin is selected from the group consisting of microcystins, nodularins, anatoxin-a, anatoxin-a(S), aplysiatoxins, cylindrospermopsins, lyngbyatoxin-a, and saxitoxins.

In certain embodiments, the toxin is selected from the group consisting of a microcystin and a nodularin.

In certain embodiments, the toxin is a microcystin.

In another aspect, there is provided herein a kit for the detection of toxic cyanobacteria in a sample, the kit comprising at least one a protein capable of conjugating with the ADDA region of microcystin designed to detect toxin-associated antibodies in a sample.

In certain embodiments, the kit further comprises a labeled antibody capable of detecting any bound anti-ADDA antibodies from the sample.

In another aspect, there is provided herein use of a kit for the detection of the presence of microcystin-producing toxic cyanobacteria in a sample.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART

DETAILED DESCRIPTION OF THE INVENTION

Described herein is a method for the detection of antibodies against the ADDA region of microcystins/nodularins in blood of exposed individuals.

Also described herein is a method of measuring host antibodies (e.g. immune serum or plasma) against cyanotoxins such as any congener of the cyclic heptapeptide microcystin.

The presently described methods use host antibodies as a way of detecting exposure of the host to cyanotoxins, such as microcystins.

The presently described methods are useful for a diagnostic test of exposure to microcystins.

Figure 1:
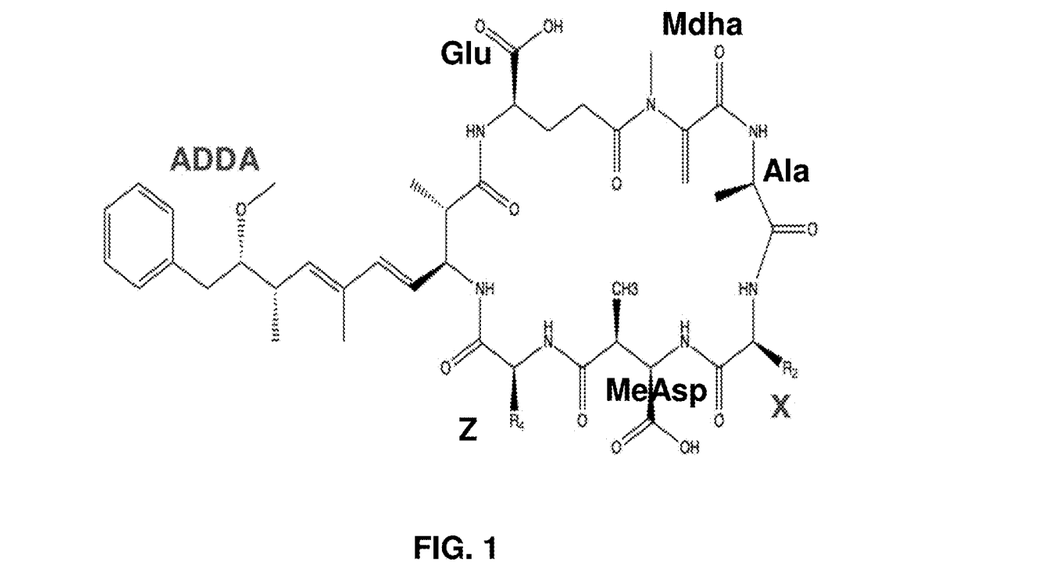
FIG. 1: Microcystin structure is a cyclic heptapeptide that contains the amino acid ADDA, a11-S,a11-E)-3-Amino-9-methoxy-2,6,8-trimethyl-10-phenyldeca-4,6-dienoic acid.

FIG. 1 shows that the microcystin structure is a cyclic heptapeptide that contains the unusual amino acid ADDA. There are more than 150 identified that vary in positions X and Z, as well by methylation, hydroxylation, or epimerization. The most common is MC-LR. Table 1 below shows certain MC variants:

TABLE 1

| MC variant | X | Z |
| --- | --- | --- |
| MC-LR | L-Leu | R-Arg |
| MC-RR | R-Arg | R-Arg |
| MC-LA | L-Leu | A-Ala |
| MC-LF | L-Leu | F-Phe |
| MC-LW | L-Leu | W-Trp |
| MC-YR | Y-Tyr | R-Arg |

Described herein is a method of measuring host antibodies (e.g. immune serum or plasma) against cyanotoxins such as any congener of the cyclic heptapeptide microcystin.

One aspect of this method is the ability to use host antibodies as a way of detecting exposure of the host to cyanotoxins (such as microcystins) as a diagnostic test of exposure.

Figure 2:
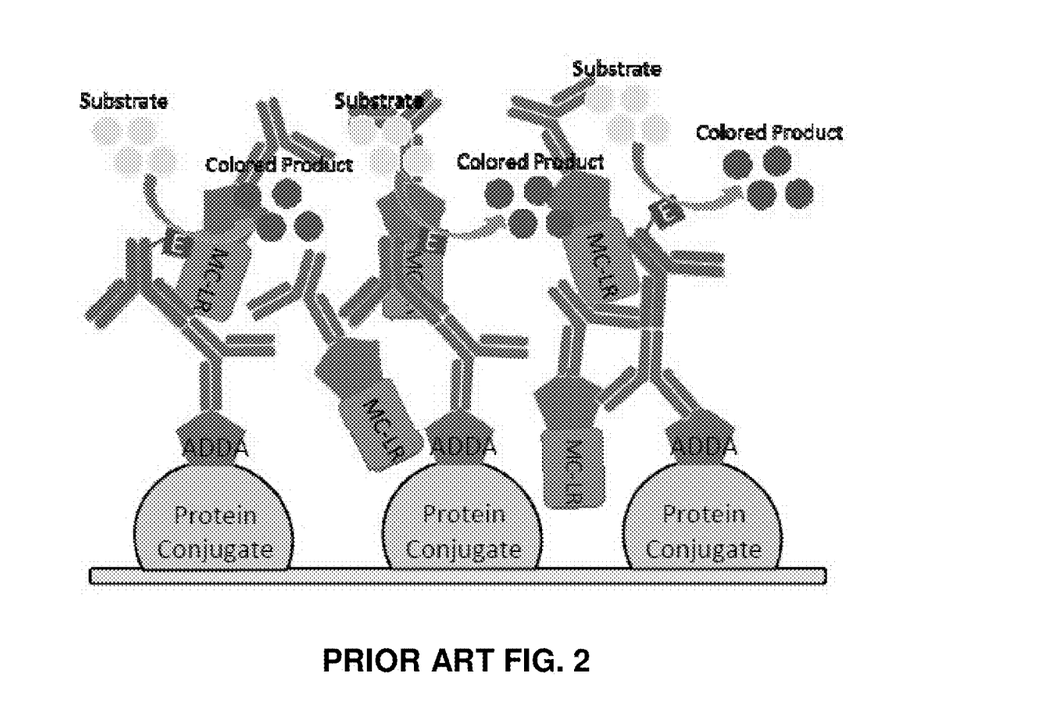
FIG. 2: Schematic illustration of a current ELISA method to detect MC toxins themselves.

PRIOR ART FIG. 2 is a schematic illustration of a currently available ELISA method to detect MC toxins themselves. The amount of signal generated is inversely proportional to the amount of free microcystin toxin that is present in the sample because it binds to the antibody and is washed away.

Figure 3:
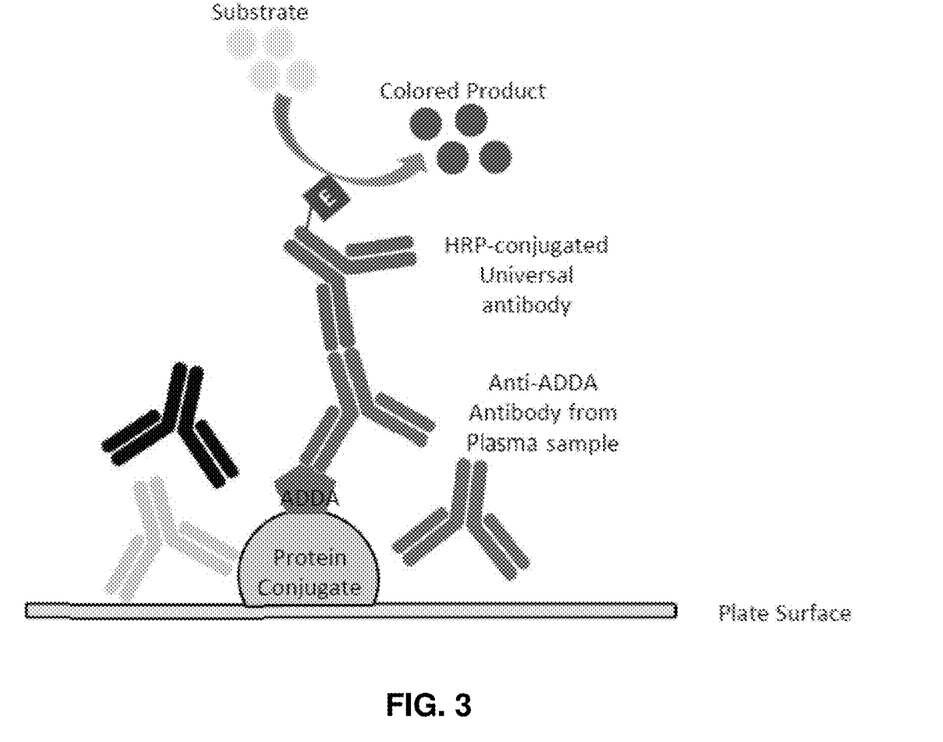
FIG. 3: Schematic illustration of presently described modified ELISA method which detects antibodies to the toxin, not the toxin itself.

In contrast, FIG. 3 shows a schematic illustration of presently described modified ELISA method which detects antibodies to the toxin, not the toxin itself. The amount of signal generated is directly proportional to the amount of ADDA-reactive antibodies present in the sample because it binds to the immobilized ADDA group on the plate and is not washed away.

One method for measuring antibodies for cyanotoxins is to react serial dilutions of serum or plasma with an immobilized cyanotoxin of interest (e.g., microcystin); for example, on a micro-titer plate. After the reaction and washing steps, secondary reagents (such as secondary antibodies and enzyme complexes which aid in visualization of the reaction) which detect the presence of the antibody of interest which is bound in complex to the immobilized cyanotoxin on the micro-titer plate. The reaction in the micro-titer plate is then read by a detector capable of detecting the reaction (e.g. by change in light absorbance).

In one example, plasma from mice exposed to the cyanotoxin microcystin-LR was compared to control mice which had not been exposed to microcystin-LR. The dilution series of plasma from the microcystin treated mice demonstrated higher levels of antibody complexed to the immobilized microcystin-LR vs control plasma, showing that this method detects antibodies against the cyanotoxin microcystin-LR.

The method is suitable for testing plasma or serum samples and can detect exposure to cyanotoxins such as microcystin and is useful in the differential diagnosis of patients with potential exposure to cyanotoxins.

The method measures a specific by-product of cyanotoxins, namely antibodies made against them by the host, which can be present days, weeks, or even longer after cyanotoxin exposure.

In order for a host to generate an immune response to a foreign antigen such as a peptide, it was previously believed that the antigen needs to be at least 9-15 linear amino acids to bind in the MHC cleft of antigen-presenting cells.

It is now shown herein, the contrary where cyanotoxins such as microcystins which only contain 7 modified amino acids in a cyclic, non-linear structure, generate an immune response, which can, in turn, be measured. Thus, it would not be readily obvious that such peptides would permit an immune reaction capable of generating antibodies.

Examples

The presently described method measures a specific by-product of cyanotoxins, namely antibodies made against them by the host, which can be present days, weeks, or even longer after cyanotoxin exposure.

Thus, even if a patient presents to a health care provider after the toxin itself is no longer detectable in biological fluids (as measure by methods such as mass spectrometry or ELISA), the disclosed test is designed to be able to help determine exposure.

Figure 4:
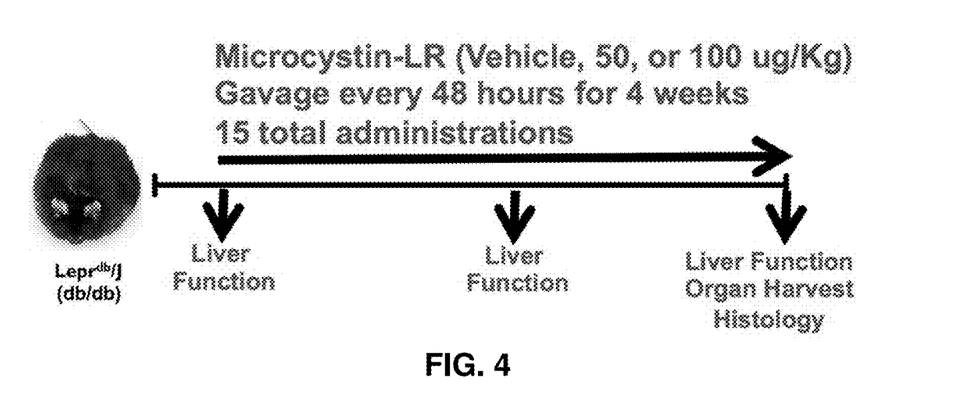
FIG. 4: Schematic illustration of a test procedure for performing an in vivo proof-of-concept study of exposure to low-dose microcystin-LR (e.g., measuring "No Observed Adverse Effect Level" (NOAEL)).

Mouse Model of Exposure:

The current No Observed Adverse Effect Level (NOAEL) of 40 µg/Kg (91 days) or 200 ug/Kg (14 days) used to derive safe exposure guidelines for microcystin. The experiments herein used 50 and 100 ug/Kg for 15 doses over 4 weeks— approximately 2.4 to 4.8 times below total NOAEL exposure. See FIG. 4.

The method of testing was as follows:
1) ELISA strips coated with a protein conjugated with the ADDA region of the Microcystin toxin (from Abraxis anti-ADDA ELISA kit) was blocked with either 3% BSA or 5% Skim Milk overnight;
2) Appropriate dilutions of plasma from either control or MC-LR exposed mice was added to the respective wells;
3) Excess plasma was washed off and the bound anti-ADDA antibodies from the plasma were detected using a Universal Ig antibody labelled with HRP (horseradish peroxidase); and,
4) Streptavidin substrate was added to give a colored product which was quantitated by reading the absorbance at 450 nm.

Figure 5:
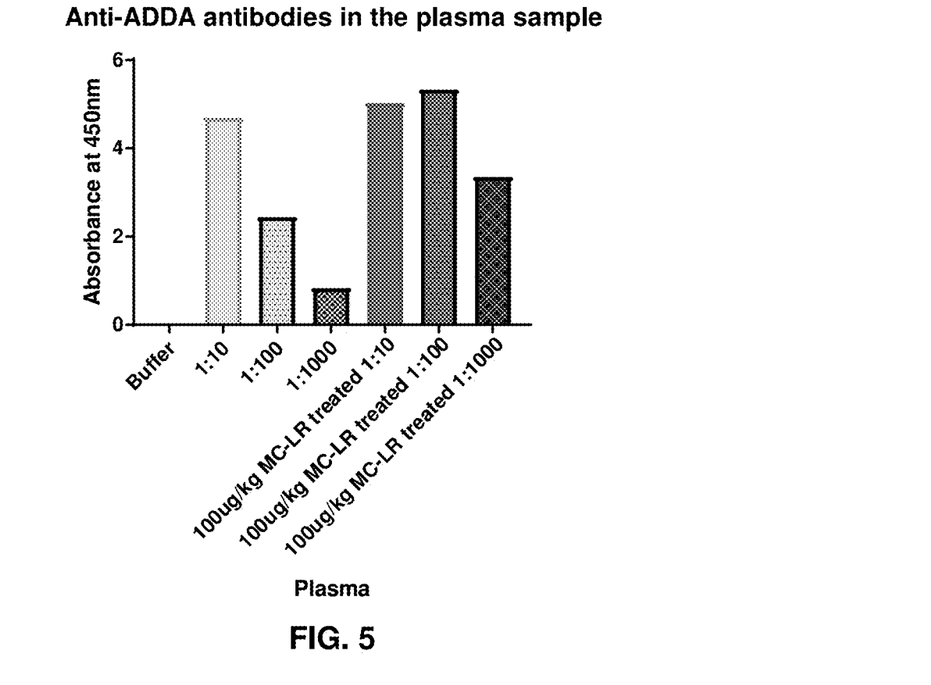
FIG. 5: Anti-ADDA antibodies in a plasma sample, where 3% BSA is used as the blocking reagent.

FIG. 5 is a graph showing the anti-ADDA antibodies in a plasma sample, where 3% BSA is used as the blocking reagent.

Figure 6:
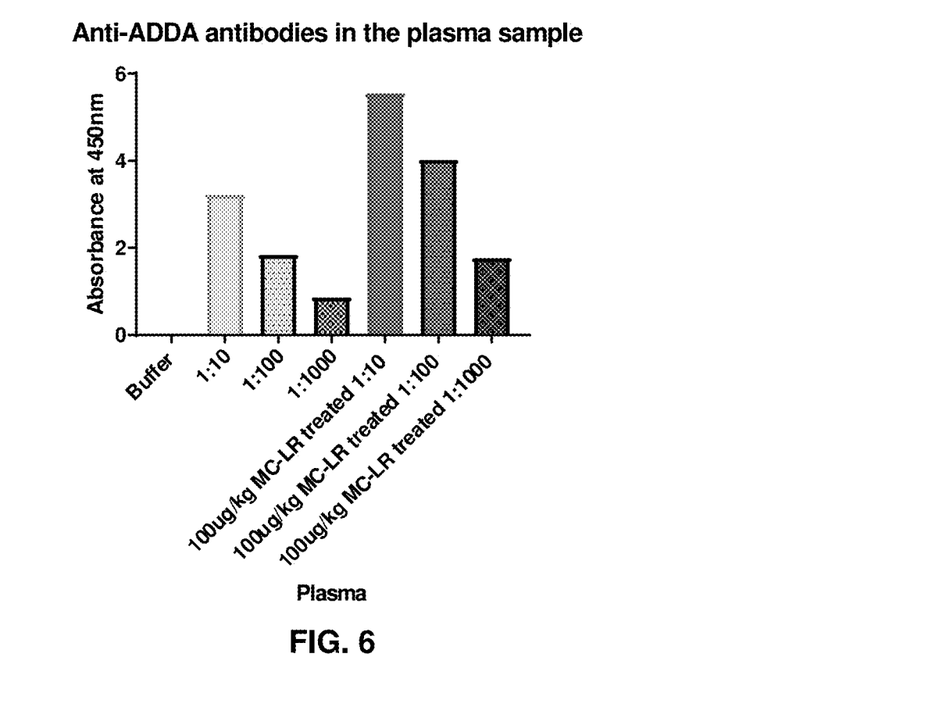
FIG. 6: Anti-ADDA antibodies in a plasma sample, where 5% Skim Milk is used as the blocking reagent.

FIG. 6 is a graph showing the anti-ADDA antibodies in a plasma sample, where 5% Skim Milk is used as the blocking reagent.

The percent increase in signal over control plasma is shown in Table 2 below:

TABLE 2

| Dilution | BSA block | Skim Milk block |
| --- | --- | --- |
| 1:10 | 7% | 72% |
| 1:100 | 119% | 119% |
| 1:1000 | 302% | 105% |

These results show that the presence of anti-ADDA antibody is detectable in plasma samples from exposed mice.

Figure 7:
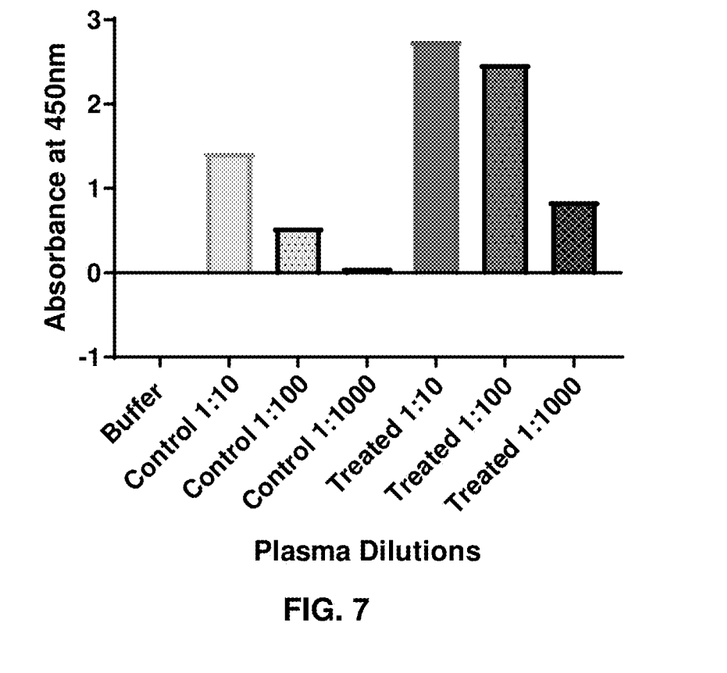
FIG. 7: Plasma from NAFLD mice exposed with 100 μg/kg of MC-LR showed a much higher signal (Green bars) as compared to control mice exposed to saline (yellow bars) indicating presence of ADDA-specific antibodies.

FIG. 7 shows that plasma from NAFLD mice exposed with 100 µg/kg of MC-LR showed a much higher signal (Green bars) as compared to control mice exposed to saline (yellow bars) indicating presence of ADDA-specific antibodies. For this experiment, blocking was done overnight with 5% skim milk.

The previous experiments used plasma from mice (exposed with 100 µg/kg MC-LR) that had pre-existing liver disease (AKA Non-Alcoholic Fatty Liver Disease or "NAFLD model". In order to extend these findings into normal healthy settings, normal mice on the C57Bl/6J background (same background as the NAFLD model but without liver disease), were exposed with 100 µg/kg MC-LR (vs saline control) and the plasma was used for the subsequent experiments.

Figure 8:
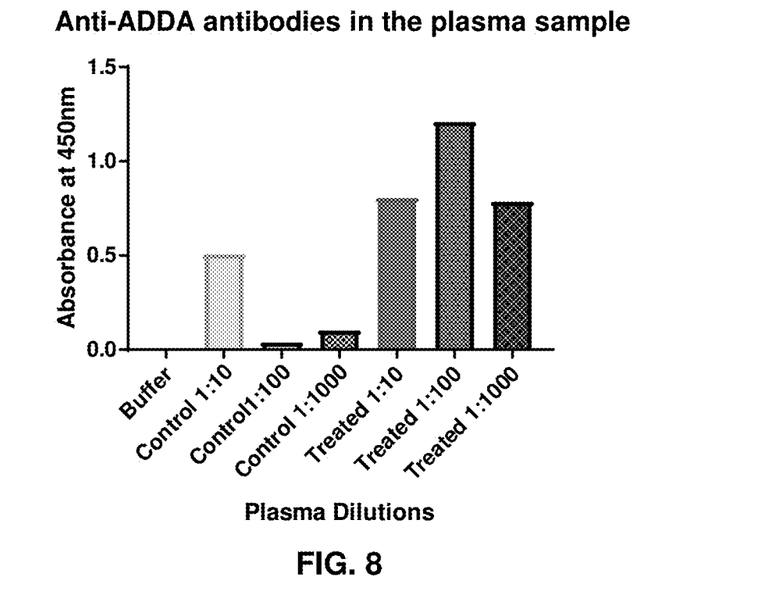
FIG. 8: Plasma from normal C57Bl/6J MC-LR exposed mice (Green Bars) also showed a much higher signal as compared to saline exposed mice (Yellow bars) indicating presence of ADDA-specific antibodies.

FIG. 8 shows that plasma from normal C57Bl/6J MC-LR exposed mice (Green Bars) also showed a much higher signal as compared to saline exposed mice (Yellow bars) indicating presence of ADDA-specific antibodies.

Varying the Time Required for Blocking the Plates with 5% Skim Milk

Figure 9:
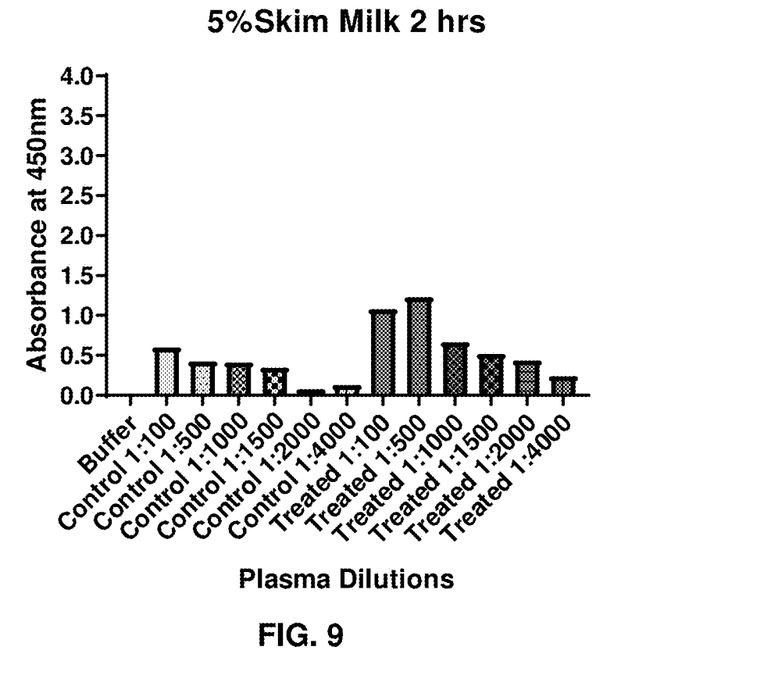
FIG. 9: Anti-ADDA antibodies in a plasma sample, where 5% Skim Milk is used as the blocking reagent after a 2 hour incubation.
Figure 10:
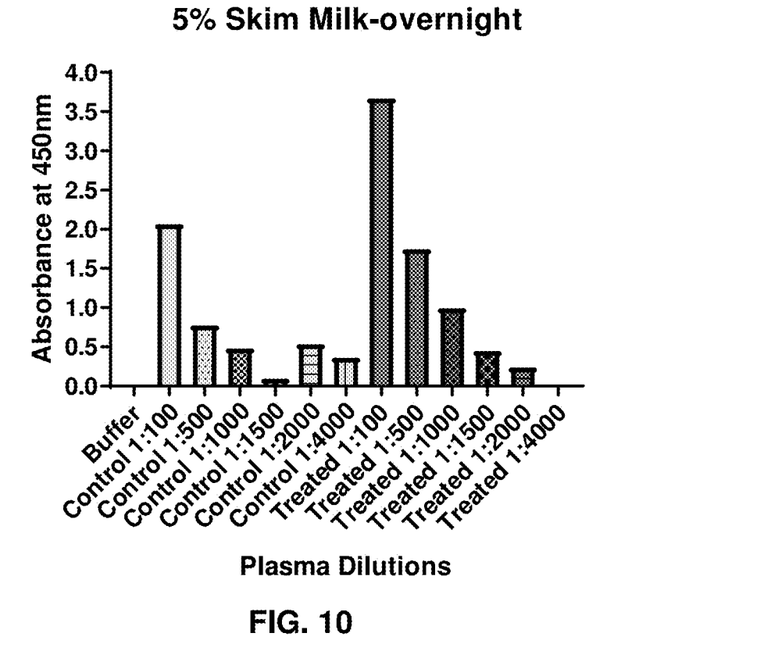
FIG. 10: Anti-ADDA antibodies in a plasma sample, where 5% Skim Milk is used as the blocking reagent after an overnight (18 hour) incubation.

Blocking the plate with 5% Skim milk overnight (FIG. 10) shows a robust increase between Control and Treated samples vs 2 hour incubation. MC-LR exposed mice (Green Bars) vs saline exposed mice (Yellow bars). FIG. 9 shows a 2 hour incubation with 5% milk FIG. 10 shows an overnight (18 hour) incubation with 5% milk.

Figure 11:
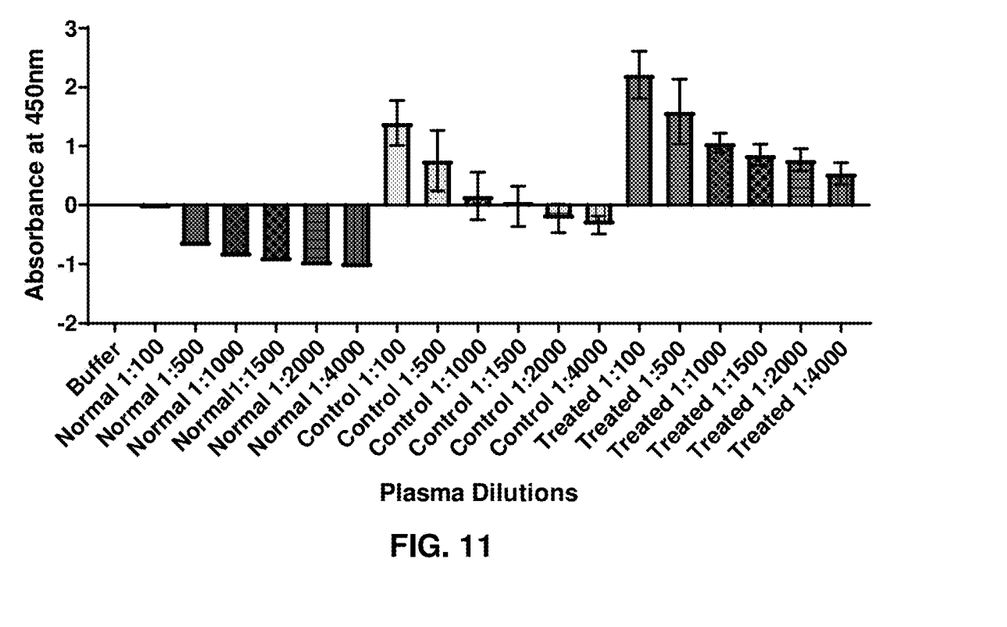
FIG. 11: Plasma samples from different saline exposed C57Bl/6J mice (n=4, yellow bars) and MC-LR exposed (n=7, green bars) C57Bl/6J mice were compared to the plasma obtained from C57Bl/6J mice from a separate unexposed colony (purple bars).

FIG. 11 shows after method optimization, plasma samples from different saline exposed C57Bl/6J mice (n=4, yellow bars) and MC-LR exposed (n=7, green bars) C57Bl/6J mice were compared to the plasma obtained from C57Bl/6J mice from a separate unexposed colony (purple bars). Data indicates that MC-LR exposed mice develop measurable antibody response which can be distinguished from various untreated control mice.

These results confirm the presence of anti-ADDA antibody can be detectable in plasma samples from exposed mice in both healthy and pre-existing liver disease settings. Blocking the plate overnight (18 hrs) with 5% skim milk showed a robust increase and difference in the signal during optimization vs 2 hour incubation.

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method for detecting exposure to a cyanotoxin, the method comprising: analyzing a sample from a host for the presence of antibodies raised in the host, wherein the presence of the antibodies is indicative of exposure to a cyanotoxin, and wherein the antibodies are against the ADDA region of a microcystin or a nodularin.

2. A method for detecting exposure to a cyanotoxin in an assay, comprising: analyzing a sample with an ELISA method for the presence of ADDA-specific antibodies complexed to an immobilized microcystin, wherein the sample comprises blood of a subject suspected of being exposed to microcystin, and the presence of the antibodies is indicative of exposure by the subject to microcystin.

3. The method of claim 1, wherein the sample comprises blood of the host, and the host is suspected of being exposed to cyanobacteria.

4. The method of claim 1, wherein the exposure is from salt water or freshwater.

5. The method of claim 1, wherein the exposure is from a blue-green algal bloom.

6. The method of claim 1, wherein the sample is taken days, weeks, or longer after cyanotoxin exposure.

7. The method of claim 1, wherein the cyanotoxin is selected from the group consisting of microcystins, nodularins, anatoxin-a, anatoxin-a(S), aplysiatoxins, cylindrospermopsins, lyngbyatoxin-a, and saxitoxins.

8. The method of claim 1, wherein the cyanotoxin is selected from the group consisting of a microcystin and a nodularin.

9. The method of claim 1, wherein the cyanotoxin is a microcystin.

10. The method of claim 2, wherein the sample is taken days, weeks, or longer after microcystin exposure.

* * * * *